US005179422A

United States Patent [19]
Peterson

[11] Patent Number: 5,179,422
[45] Date of Patent: Jan. 12, 1993

[54] CONTAMINATION DETECTION SYSTEM

[75] Inventor: Lauren M. Peterson, Ann Arbor, Mich.

[73] Assignee: Environmental Research Institute of Michigan, Ann Arbor, Mich.

[21] Appl. No.: 700,441

[22] Filed: May 15, 1991

[51] Int. Cl.⁵ ............................................. G01N 21/88
[52] U.S. Cl. ..................................... 356/239; 250/572
[58] Field of Search ................ 356/237, 239; 250/562, 250/563, 572, 339

[56] References Cited

U.S. PATENT DOCUMENTS

| 4,689,491 | 8/1987 | Lindow et al. ...................... 250/572 |
| 4,764,676 | 8/1988 | Doyle .............................. 250/339 X |
| 5,002,391 | 3/1991 | Wolfrum et al. ................. 250/339 X |
| 5,017,787 | 5/1991 | Sato et al. ........................ 250/339 X |

FOREIGN PATENT DOCUMENTS 1-88696  4/1989  Japan .................................. 356/237

OTHER PUBLICATIONS

Article by Beyer and Garbuny in *Applied Optics*, Jul. 1973, vol. 12, No. 7, p. 1496, entitled "Pollutant Detection by Absorption Using Mie Scattering and Topographic Targets as Retroreflectors".

*Primary Examiner*—Vincent P. McGraw
*Attorney, Agent, or Firm*—Krass & Young

[57] ABSTRACT

A system for detecting minute amounts of water contaminant in semi-conductor microelectronic integrated circuits (MIC) includes two lasers 11,12 producing electromagnetic radiation at two discrete wavelengths. Each laser beam being sent through a chopper 13 and 14 respectively and combined via mirror 16 and beam splitter 17 to form a single two part beam along optical axis 22. The beam passes through a reflective beam splitter 26, a quarter wave plate 28 and lens 29 to be directed to a MIC 31 that is mounted onto drive mechanisms 31 and 32. Diffuse reflections from the bottom of the MIC or specular reflections from metallization layers pass back through MIC 31, lens 29, quarter wave plate 28, beam splitter 27 and through lens 48 to detector 47 which compares the intensity of the radiation at the two wavelengths with the intensities of the wavelengths as detected by detector 21 through a lock-in amplifier 49.

7 Claims, 3 Drawing Sheets

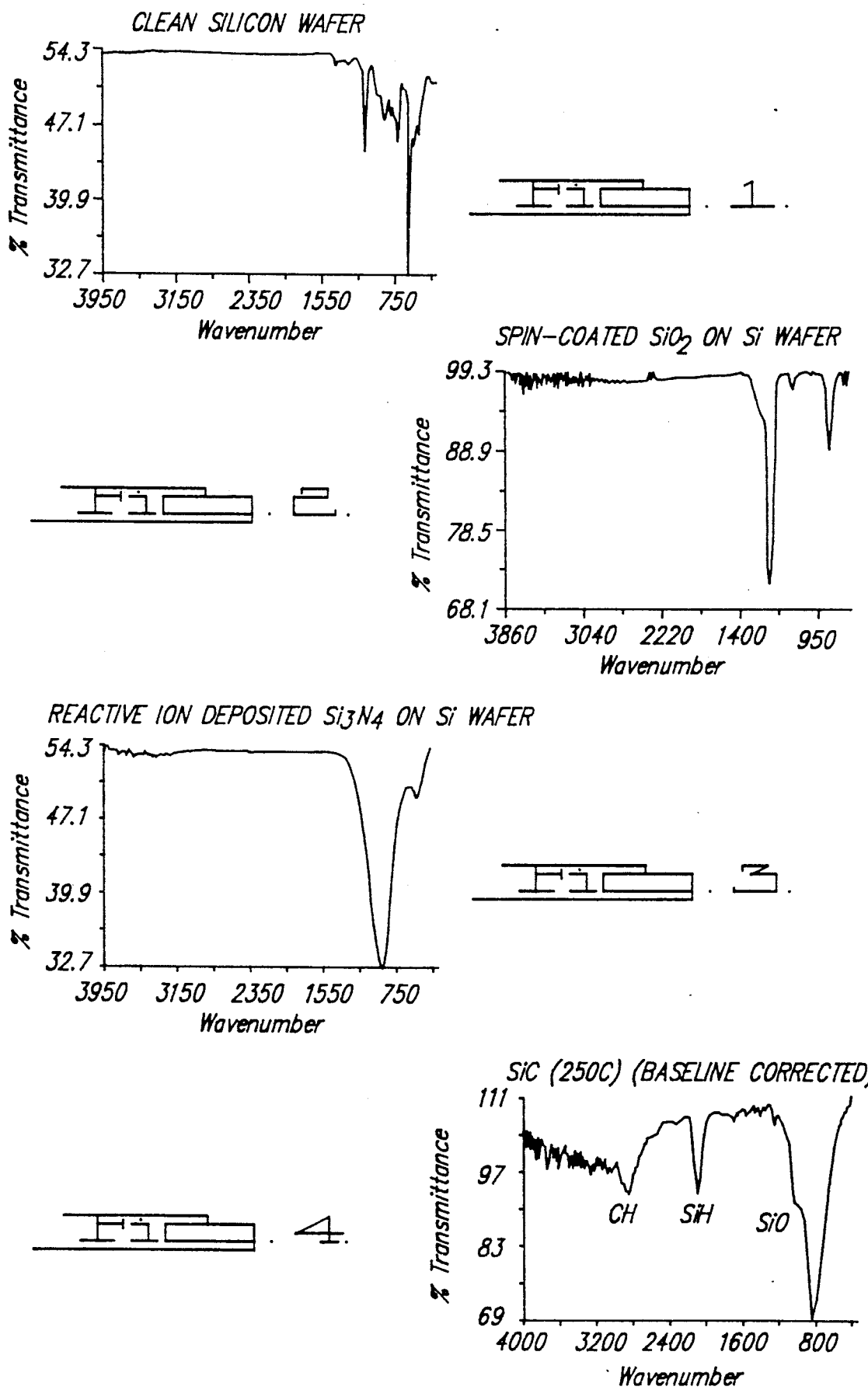

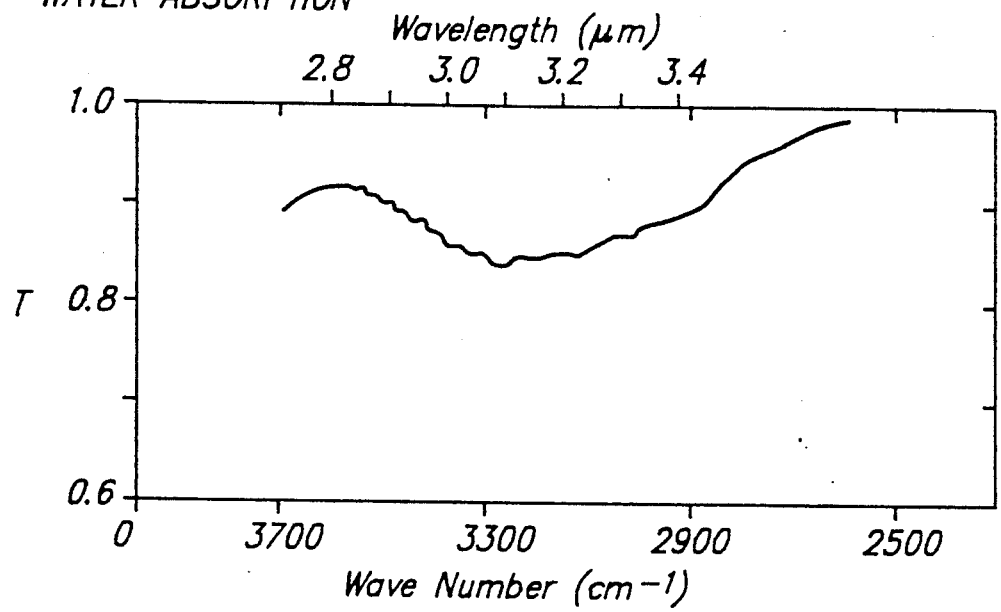
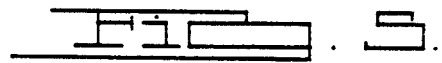
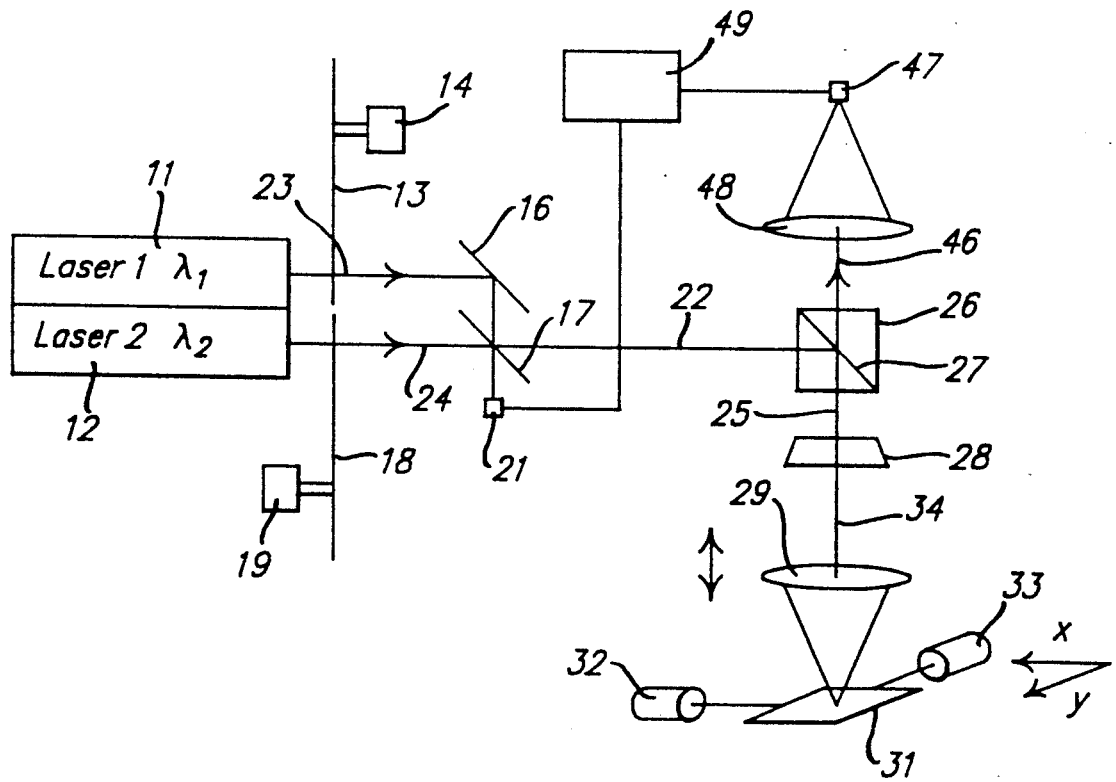
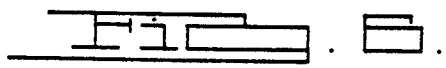

CONTAMINATION DETECTION SYSTEM

TECHNICAL FIELD

This invention relates to the detection of contaminating material in a sample and, in particular, to the detection of trace amounts of water in semiconductors for use in a microelectronic integrated circuit.

BACKGROUND OF THE INVENTION

The presence of even minute quantities of water in contact with metallized areas of a semiconductor device can lead to corrosion of the metal and failure of the component. Manufacturers of these devices attempt to prevent contamination by coating them with layers of passivating material, but such layers can have defects through which water can penetrate. The amounts of water able to pass through the defects are so small that it is difficult to detect their presence. Feature dimensions of semiconductor devices may be on the order of a micron, and water that has to be detected may be distributed within the hygrometric $SiO_2$ planarizing layer which is usually deposited before the passivation layers. The water may form thin pools only a few microns in lateral extent and only a fraction of a micron deep. The volume in such a pool is on the order of a cubic micron, which is about a picogram of liquid water. Detection of such localized regions of water requires the use of microprobe techniques, but since these regions can be anywhere on the semiconductor device, every microscopic area must be examined, which makes it necessary to scan the entire surface of the device, area by area.

It is typical to form such devices on silicon wafers having a diameter of about 10 cm. and each device may be about 5 mm. sq. It would not be commercially acceptable to have to spend too much time in the water-detection process, and each individual measurement of an incremental area needs to be carried out in about 1 millisecond.

Neither Raman scattering nor nuclear resonance techniques are sensitive enough to detect such small quantities of water, but water does have strong radiation absorption bands in the region of 2.7 $\mu$m to about 3.5 $\mu$m, which makes infrared testing a possibility. Standard types of infrared testing by means of a grating or even a Fourier transform instrument capable of generating a full spectrum could be used to detect the presence of water in semiconductor devices, but their use would be too time-consuming.

SUMMARY OF THE INVENTION

One aspect of the invention is to detect the presence of minute amounts of an impurity or contaminant in a sample made from a host material by microprobe examination using electromagnetic radiation of two distinct wavelengths focussed onto the sample.

Another aspect of the invention is to detect the absorption of the laser beam in a material contaminated with contaminant by comparing the absorption of energy in a beam having a wavelength known to be absorbed by the contaminant with the absorption of energy in a second beam having a wavelength slightly different but enough so to be outside of any absorption band of the contaminant.

A further aspect of the invention is to use beams that are substantially equally absorbed, if at all, by other non-contaminating materials along the optical path shared by both beams.

The present invention is based on the fact that for materials of interest in a physical device, such as a semiconductor device, wavelength regions can be found that are transparent in an uncontaminated device but are absorbing when the contaminant, such as water, is present.

In accordance with this invention, an infrared beam preferably having two wavelength components is generated by a single laser or by more than one laser, and the differential absorption of these components is measured to detect the presence of a material that would absorb one wavelength more than it would the other. Whether the beam components are generated in one laser or two, they share an optical axis through a beam splitter, and the beam passes through a lens that focuses both components on a sample that is transparent to, or at least partially transmits, both beams. The contaminating material, if present, may be on or in the sample.

Preferably, on the far side of the sample from the source of the laser beam is a surface that reflects the beam back through the sample and through any contaminating material encountered in the initial passage. The reflected beam then passes back through the lens along the optical path to the beam splitter, which directs the reflected beam to a detector that separately measures the intensity of the energy in each wavelength component and compares the intensities. If the component that would be absorbed by the contaminating material has been reduced more than the other component, it is because some contaminating material is present in the examined part of the sample. The amount of reduction can be measured to determine whether the amount of contaminating material is great enough to warrant scrapping the sample.

The two-component laser beam can be produced by two separate lasers directing their beams through an optical combiner, which may include one or more partially transmitting mirrors. Alternatively, the two components can be generated in a single laser tunable to the two desired wavelengths. Fortunately, there are lasers known as color center lasers that are capable of tuning to two usable wavelengths of around 3 $\mu$m where absorption bands of water are located. The tuning range is great enough so that one color center laser can be tuned back and forth to generate a beam having a wavelength just outside a water absorption band and then one within it.

The testing procedure must be carried out over the entire surface of the sample, and this is preferably done by effecting scanning movement of the sample relative to the beam to cause the beam to be focussed on each incremental area of the sample. If the two beam components are present simultaneously, the scanning can proceed from point to point along a suitable path, such as a raster scan. If the two wavelengths are generated by the same laser, it must be done in sequence. Either the beam must be held stationary on one point long enough to tune from one wavelength to the other, or some area of the sample must be scanned with the laser tuned to generate a beam at one of the wavelengths, and then the same area must be rescanned after the laser has been tuned to the other wavelength. In that case, it is essential that exactly the same area be scanned by beams of both wavelengths so that the comparison of the reductions in intensity can be compared for each incremental area of the sample.

BRIEF DESCRIPTION OF THE DRAWINGS

FIGS. 1-4 are graphs showing the transmittance of the silicon substrate and passivating layers of a semiconductor device;

FIG. 5 is a graph showing the absorption of water in a thin film of $MgF_2$ over the wavelength region of about 2.7 μm to about 4.0 μm;

FIG. 6 is a schematic representation of one embodiment of a contamination detection system in accordance with this invention;

DESCRIPTION OF PREFERRED EMBODIMENTS OF THE INVENTION

Figure 7:
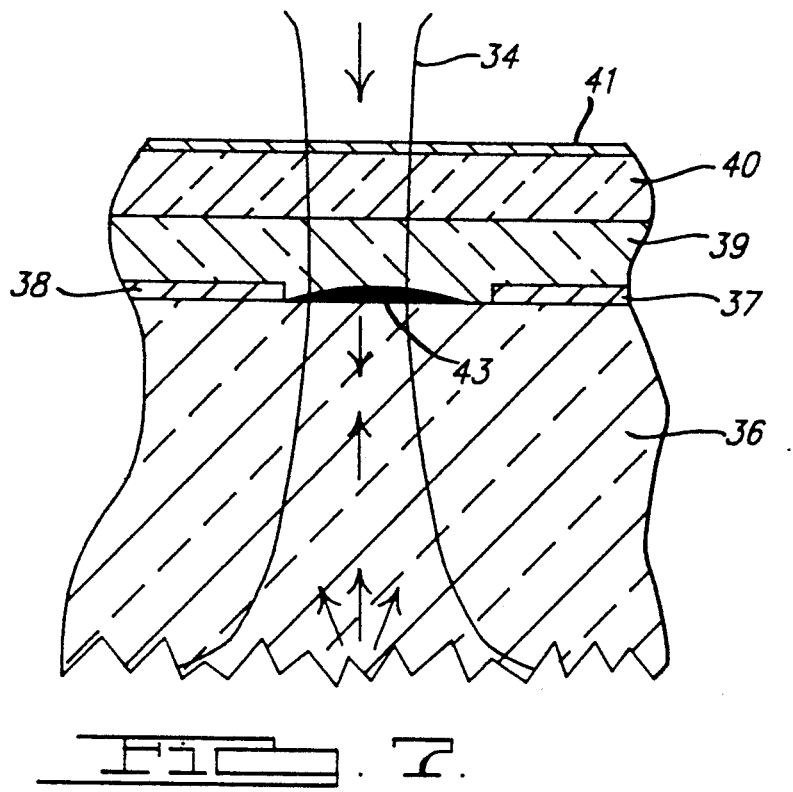
FIG. 7 is a magnified cross-sectional representation of a semiconductor device with the beam in FIG. 6 passing through it.

FIG. 1 shows that a clean silicon wafer, which is commonly used as the substrate for semiconductor devices, has a virtually constant transmittance of electromagnetic energy from a wavenumber as high as 3950 $cm^{-1}$ to a wavenumber of about 1550 $cm^{-1}$. The same is true of $SiO_2$, as shown in the graph in FIG. 2, and $Si_3N_4$, as shown in the graph in FIG. 3. Both of these materials are deposited as thin layers on the surface of the substrate in forming semi-conductor devices, as is SiC, the transmittance graph for which is shown in FIG. 4. While the transmittance of SiC is not as uniform over as wide a range of wavelengths, it is still substantially uniform in the infrared region of interest. This region extends from approximately 3000 $cm^{-1}$ to approximately 3300 $cm^{-1}$ and is the region in which water has a substantial absorption of electromagnetic energy, as shown in the graph in FIG. 5.

FIG. 6 shows apparatus for making use of the characteristics of the materials used in semiconductors and the characteristics of water, a major contaminating material, to detect the presence of this contaminating material in order to separate out semiconductor devices impaired by it. The apparatus includes a first laser 11 that produces a beam having a wavelength of about 3.1 μm (wavenumber 3200 $cm^{-1}$) and a second laser 12 that produces a beam having a wavelength of about 2.8 μm (wavenumber 3600 $cm^{-1}$) The beam of electromagnetic energy from the first laser passes through openings in a first chopper blade 13 rotated by a motor 14, and the resulting chopped beam is reflected by a mirror 16 set at a 45° angle to the path of the beam. The mirror reflects the beam down to an optical combiner 17 in the form of a partially-transmitting mirror that combines the beam from the first laser 11 with the beam from the second laser 12 after the latter beam has passed through openings in a second chopper blade 18 driven by a motor 19. The first beam has a resulting square wave of different frequency than the second beam.

Approximately half of the energy in the component beam from the laser 11 is reflected by the partially-transmitting mirror 17 and most of the remainder of the energy from that beam (except for the small amount absorbed in the mirror) passes straight through to a first detector 21. Conversely, half the energy in the beam produced by the second laser 12 is reflected to the detector 21 by the partially-transmitting mirror 17 and the remainder (except for a small loss) is combined with the beam from the laser 11 to form a combined beam consisting of the two wavelength components. The combined beam travels along the optical axis 22 which is which is really a continuation of the laser beam from laser 11 along optical axis 23 and the laser beam from laser 12 along the optical axis 24.

In this embodiment of the invention, the combined laser beam along optical axis 22 impinges on a beam splitter 26 that includes a reflective surface 27 positioned at 45° with respect to the beam to reflect the two-component beam perpendicularly downward along an optical axis 25. For the purpose of clarity in the description hereinafter of another part of the apparatus in FIG. 6, the path followed by both components of the combined beam from their origins at the lasers 11 and 12 to the beam splitter 26 is called the first path. In the preferred embodiment, the beam splitter 26 is a polarization splitter linearly polarized in the same plane as both components of the laser beam traveling along the first path. The beam splitter can however also be a partially-transmitting mirror. Use of a polarization splitter allows substantially all of the energy in the beam to be reflected by the surface 27 to proceed directly downward.

A quarter-wave plate 28 is located on the optical axis log 25 below the beam splitter, and is oriented so that it converts the linearly polarized beam from the polarization beam splitter 26 to a circularly polarized beam. It is in this condition that the combined beam enters a lens 29 that focuses the beam on a sample 31 such as a microelectronic integrated circuit commonly referred to as a MIC. Preferably the quarter wave plate 28 is mounted for rotation about the optical axis leg 25 so that examination of orthogonal polarization is possible. In the simplified drawing in FIG. 6, the sample is shown as a rectangular plate connected to X and Y drive means 32 and 33 respectively capable of moving the sample in incremental steps in the X and Y directions, respectively. These drive means allow the sample 31 to be moved in such a way relative to the beam focussed on it as to cause the beam 34 to cover, in time, every spot on the sample, or at least, on every spot selected by signals fed to the drive means 32 and 33.

FIG. 7 shows a greatly enlarged cross-sectional view of a fragment of the sample 31. The thickest part of the sample is the silicon substrate 36 on the upper surface of which are formed metallizations 37 and 38. A planarizing layer 39 of $SiO_2$, together with passivation layer 40 of $Si_3N_4$ and barrier layer 41 of SiC, are formed over the whole surface of the electrodes and the substrate. In spite of the protective layers, water, here illustrated as a microscopic pool 43 but which could be dispersed in the layer 39, has found entry by way of unseen defects in the protective layers. This contaminating water absorbs the 3.1 μm radiation to a measurably greater degree than it does the 2.8 μm radiation, in accordance with the relative transmittances of these components in FIG. 5.

The beam 34 is focused so that its waist is in the plane of the pool 43. The minimum diameter of this circle is determined by the wavelength of the radiation in the beam, which consists of 2.8 μm and 3.1 μm components, and is therefore on the order of 5 μm. It is desirable that the lens 29 has a relatively low f/number so as to form a small focal spot in the plane where the pool 43 is likely to be, if it is there at all. The low f/number and therefore small depth of focus may make it desirable to have an autofocus system in operation to keep the beam focused at the proper plane, particularly as the sample is moved from point to point to test every incremental area. It should be noted that the beams from the lasers 11 and 12 are relatively broad, and that the curved lines identified as the beam 34 represent the outermost rays of the beam, or its caustic surface. The f/number is a measure of how sharply these lines (really, a solid cone of rays) can be caused to converge, and this number may have any value from about f/1 to about f/11, but it is preferable that the lens have an f/number less than about f/4. The beam 34 is focussed so that it fully passes through pool 43 if pool 43 exists. By having a narrow beam pass through pool 43 the spatial resolution is enhanced.

After passing through the layers 39-41, the contaminating water in the pool 43, and the substrate 36, the beam 34 strikes the bottom surface 44, which diffuses reflected light. Some of the energy in the beam is reflected back through the substrate 36, the layers 39-41, and the water pool 43, where an additional amount of the 3.1 $\mu$m radiation is absorbed relative to the 2.8 $\mu$m radiation. The efficiency of reflection of the surface 44 can be increased by coating it with a material such as silver or gold.

If the quarter-wave plate 28 is either absent or oriented so that it provides no retardation, any specular reflection of polarized beam 34 from the smooth surfaces of the layers 39-41 and the top surface of the substrate 36 is similarly polarized, and therefore is reflected by the polarizing beam splitter 26 back to the laser. The diffuse radiation returned from the bottom surface is depolarized, and part of this radiation passes through the beam splitter 26 and emerges on a different path 46 than the first path from the lasers 11 and 12.

In this embodiment, the different path 46 is a straight continuation of the optical axis 25 extending from the sample 31 to the beam splitter with the first path or optical axis 22 being perpendicular thereto. Alternatively, it is also possible for the first path or optical axis 22 to be aligned with optical axis 25 and the different path 46 to be perpendicularly extending therefrom.

The radiation that follows the path 46 is, therefore, primarily radiation that has been differentially affected by any contamination in the sample 31. This radiation is focused on a detector 47 by a lens 48. By synchronous operation with the choppers 13 and 18, a lock-in amplifier 49 can be used to determine whether the intensity of the radiation detected by the detector 47 is due to the 3.1 $\mu$m component or the 2.8 $\mu$m component, and their relative intensities can be compared to determine the presence and approximate amount of contaminating material. A warning system can be connected to the detector to warn if the contamination is excessive.

The elimination of specular reflected light decreases the amount of radiation reaching detector 47 that did not pass through the tested area in the sample; i.e. the noise reaching detector 47 is decreased and the signal to determine the existence of pool 43 is purer.

When laser beam 34 encounters a metallization 37, it is reflected back upon itself and does not pass into substrate 36. The specularly reflected radiation remains polarized and would be reflected by beam splitter 26 along path 22 back to the lasers 11 and 12. If, however, quarter wave plate 28 is rotated to produce quarter wave retardation when beam 34 first passes through it, then the radiation reflected by the metallization is additionally retarded when it passes through quarter wave plate 28 a second time. The polarization of the resulting half wave retarded beam is therefore not reflected by beam splitter 26 but passes through along path 46 to detector 47.

For this orientation of the quarter wave plate 28, radiation 34 reflected from the metallization 37 is maximally detected by detector 47. The presence of any contaminating water in thin film layer 39 above the metallization is determined from the difference signal between wavelengths $\lambda$1 and $\lambda$2. Although undesirable specular reflections from the thin film interfaces also pass through beam splitter 26, they are weaker than the metallic reflection such that signal-to-noise ratio remains good.

The reference detector 21 is used in conjunction with detector 47 such that the intensity levels detected at detector 21 are used to determine that the initial intensities of radiation at the first wavelength is due to the contaminant and not due to a drift of intensity level produced by the lasers 11 or 12.

The square wave signals detected by detector 47 are electronically tuned to the chopped signals detected by detector 21 and compared. The use of a lock-in amplifier 49 is a useful way to narrow the frequency band of the desired square wave signal to further enhance the signal to noise ratio.

Figure 8:
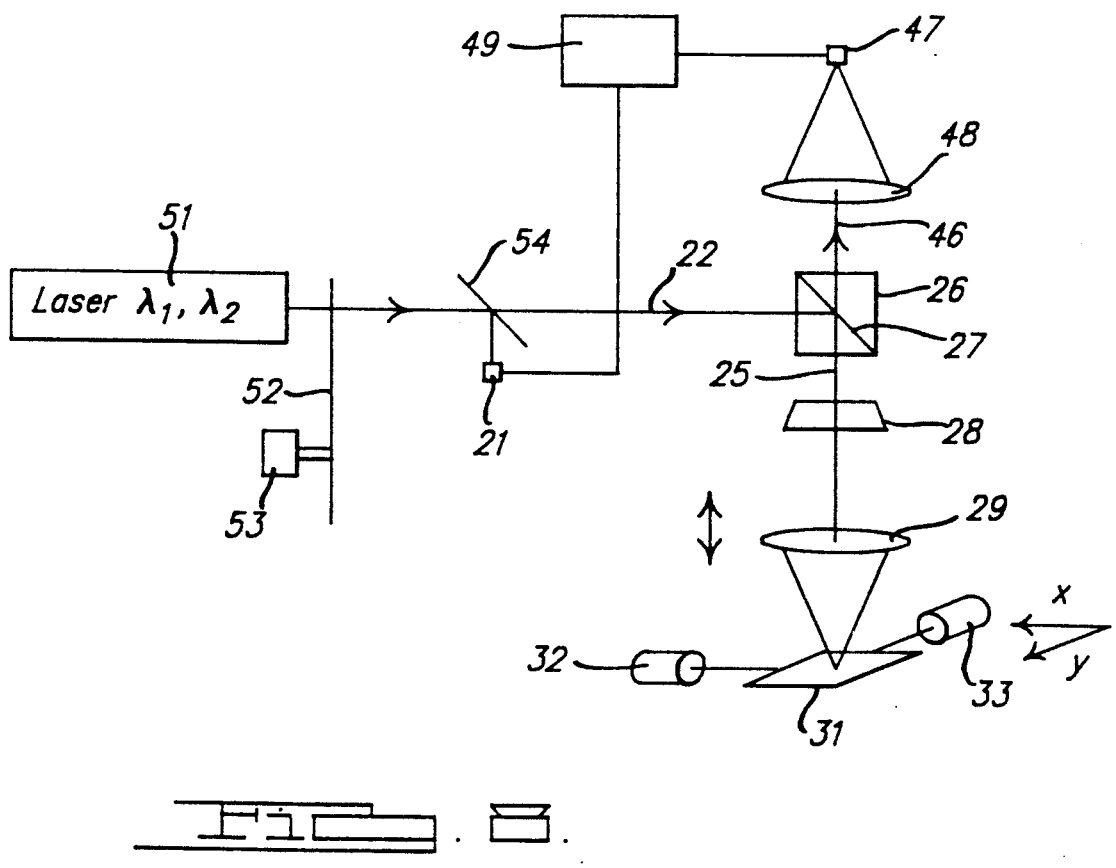
FIG. 8 is a schematic representation of another embodiment of a contamination detection system in accordance with this invention.

While the system in FIG. 6 permits each incremental area to be tested in about 1 ms., it requires the use of two separate lasers 11 and 12. By using a tunable color center laser, it is possible to make the same measurements with only one laser. Such a system is shown in FIG. 8, many of the components of which are the same as in FIG. 6 and have been given the same reference numerals.

A tunable laser 51 emits a beam having, at one time, a wavelength of 3.1 $\mu$m and, at another time, a wavelength of 2.8 $\mu$m along a first path along an optical axis 22. The beam passes through the rotating blade 52 of a chopper rotated by a motor 53 and through a partially-transmitting mirror 54. This mirror diverts only a small part of the radiation to a detector 21 that monitors the chopped laser radiation. The first path followed by the beam ends at the polarization beam splitter 26, which diverts the laser beam to cause it to pass through the quarter-wave plate 28 and be focussed on the sample 31 by the lens 29. The reflected beam passes back through the lens, the quarter-wave plate, and the polarization beam splitter, after which it follows the path 46 through the lens 48 to the detector 47.

If the laser can be tuned to the alternate wavelength and back again quickly enough, each incremental area can be examined by the wavelength components before the drive means 32 and 33 move the sample to the next location. Alternatively, it may be preferable to test for contamination at several spots, using one wavelength, and then tune the laser to the other wavelength, perhaps while it is being returned to the starting point of that series of spots, and rescan exactly those same spots with the laser tuned to the other wavelength. The number of spots that can be scanned in one series is determined in part by the accuracy of rescanning.

While this invention has been described in terms of specific embodiments for specific purposes using lasers emitting beams having specific wavelengths, it will be understood that these factors should not be considered as limiting the scope of the invention.

The lasers 11, 12 and 51 can be the continuous or pulse type. If the pulse type, the beam need not be focussed at a single point but can cover an area. The detector 47 may also be a 2-D array of detector pixels that covers a discrete area at a time from a pulsed laser. Furthermore, the beam 34 need not emanate from a laser but may emanate from a continuous wavelength electromagnetic source with appropriate filters.

A partially transmitting beam splitter may replace the polarizing beam splitter 26 or a small reflective surface can replace the splitter 26 if the path of the reflected beam off of the sample misses the reflective surface. The system may have the detector 47 placed under the sample to detect radiation passing through the sample.

Other variations and modifications of the preferred embodiments can be made without departing from the spirit and scope of the invention as defined in the following claims.

I claim:

1. A contamination detection system to test for trace amounts of a contaminating material that absorbs electromagnetic energy at a first wavelength more a greater amount than at a second wavelength in a sample made from other material that passes electromagnetic radiation at said first and second wavelengths, both wavelengths being substantially equally absorbed by said other material, the detection system comprising:

laser beam-producing means to direct a laser beam along an optical axis toward the sample, the beam including electromagnetic energy at the first and second wavelengths, said beam-producing means including
  a first laser producing a first beam having the first wavelength,
  a second laser producing a second beam having the second wavelength, and
  an optical combining means to combine the first and second beams to travel along a first path;

means on the optical axis beyond the location of the contaminating material to reflect at least a part of the beam back through the sample and the contaminating material and back along the optical axis;

polarization beam-splitting means on the optical axis between the beam-producing means and the sample, the part of the optical axis between the beam-producing means and the beam-splitting means comprising the first path;

a lens on the optical axis between the beam-splitting means and the sample for focus the beam at an aiming point on the sample and to direct reflections of the beam back along the optical axis through the beam-splitting means, the beam-splitting means splitting at least a portion of the reflected beam to follow a different path than the first path according to the polarization condition of the portion;

a quarter-wave plate on the optical axis between the beam-splitting means and the lens to modify the polarization of the beam and any reflected parts of said beam passing through the quarter-wave plate, said quarter-wave plate oriented to cause the beam from said beam-producing means to be circularly polarized and to polarize the part of said reflected beam to follow said different path; and detection means on the different path to measure the intensity of the reflected beam to determine any reduction in the intensity of the radiation at the first wavelength in comparison to any reduction in the intensity of the radiation at the second wavelength.

2. A contamination detection system to test for trace amounts of a contaminating material that absorbs electromagnetic energy at a first wavelength more highly than a second wavelength in a sample at least a portion of which is substantially transparent to electromagnetic radiation at the first and second wavelengths, the detection system comprising:

laser beam-producing means to direct a laser beam along an optical axis toward the sample, the beam including electromagnetic energy having said first and second wavelengths, said beam-producing means including
  a first laser producing a first beam having the first wavelength,
  a second laser producing a second beam having the second wavelength, and
  an optical combining means to combine the first and second beams to travel along a first path; an optical chopping means including
  a first optical chopper between the first laser and the optical combining means to intercept the first beam according to a first timing pattern, and
  a second optical chopper between the second laser and the optical combining means to intercept the second beam according to a second timing pattern;

means beyond the sample to reflect at least a part of the beam back through the sample and back along the optical axis;

beam-splitting means on the optical axis between the beam-producing means and the sample, the part of the optical axis between the beam-producing means and the beam-splitting means comprising the first path;

lens means on the optical axis between the beam-splitting means and the sample for focus the beam at an aiming point on the sample and to direct reflections of the beam back along the optical axis through the beam-splitting means, the beam-splitting means splitting at least a portion of the reflected beam to follow a different path than the first path; and detection means on the different path to measure the intensity of the reflected beam to determine any reduction in the intensity of the radiation at the first wavelength in comparison to any reduction in the intensity of the radiation at the second wavelength.

3. A contamination detection system to test for trace amounts of a contaminating material that absorbs electromagnetic energy at a first wavelength more highly than a second wavelength in a sample at least a portion of which is substantially transparent to electromagnetic radiation at the first and second wavelengths, the detection system comprising:

laser beam-producing means to direct a laser beam along an optical axis toward the sample, the beam including electromagnetic energy having said first and second wavelengths, said beam-producing means including
  a first laser producing a first beam having the first wavelength,
  a second laser producing a second beam having the second wavelength, and
  an optical combining means to combine the first and second beams to travel along a first path;

a reference radiation detector means located in a position relative to the optical combining means to receive radiant energy that is not directed along the first path by the optical combining means;

means beyond the sample to reflect at least a part of the beam bach through the sample and back along the optical axis;

beam-splitting means on the optical axis between the beam-producing means and the sample, the part of the optical axis between the beam-producing means and the beam-splitting means comprising the first path;

lens means on the optical axis between the beam-splitting means and the sample for focus the beam at an aiming point on the sample and to direct reflections of the beam back along the optical axis through the beam-splitting means, the beam-splitting means splitting at least a portion of the reflected beam to follow a different path than the first path; and detection means on the different path to measure the intensity of the reflected beam to determine any reduction in the intensity of the radiation at the first wavelength in comparison to any reduction in the intensity of the radiation at the second wavelength.

4. A contamination detection system to test for trace amounts of a contaminating material that absorbs electromagnetic energy at a first wavelength more highly than a second wavelength in a sample at least a portion of which is substantially transparent to electromagnetic radiation at the first and second wavelengths, the detection system comprising:

radiation beam-producing means to direct a radiation beam along an optical axis toward the sample, the beam-producing means being tunable between the first and second wavelengths;

means beyond the sample to reflect at least a part of the beam back through the sample and back along the optical axis;

beam-splitting means on the optical axis between the beam-producing means and the sample, the part of the optical axis between the beam-producing means and the beam-splitting means comprising the first path;

lens means on the optical axis between the beam-splitting means and the sample for focus the beam at an aiming point on the sample and to direct reflections of the beam back along the optical axis through the beam-splitting means, the beam-splitting means splitting at least a portion of the reflected beam to follow a different path than the first path;

detection means on the different path to measure the intensity of the reflected beam to determine any reduction in the intensity of the radiation at the first wavelength in comparison to any reduction in the intensity of the radiation at the second wavelength;

first scanning means to cause relative translation between the sample and the beam in a first direction transverse to the optical axis;

second scanning means to cause relative translation between the sample and the beam in a second direction transverse to both the second direction and the optical axis;

means connected to said second scanning means to limit its scanning movement in the second direction to a predetermined distance defining a scanned region while the laser is tuned to the first wavelength; and means connected to said second scanning means to cause said second scanning means to repeat its scanning movement over the scanned region while the laser is tuned to the second wavelength.

5. A contamination detection system to test for trace amounts of a contaminating material that absorbs electromagnetic energy at a first wavelength more highly than a second wavelength in a sample at least a portion of which is substantially transparent to electromagnetic radiation at the first and second wavelengths, the detection system comprising:

radiation beam-producing means to direct a radiation beam along an optical axis toward the sample, the beam-producing means being tunable between the first and second wavelengths;

means beyond the sample to reflect at least a part of the beam bach through the sample and back along the optical axis;

beam-splitting means on the optical axis between the beam-producing means and the sample, the part of the optical axis between the beam-producing means and the beam-splitting means comprising the first path;

lens means on the optical axis between the beam-splitting means and the sample for focus the beam at an aiming point on the sample and to direct reflections of the beam back along the optical axis through the beam-splitting means, the beam-splitting means splitting at least a portion of the reflected beam to follow a different path than the first path, said lens means having an f-number not substantially less than 1 and not substantially greater than 11; and detection means on the different path to measure the intensity of the reflected beam to determine any reduction in the intensity of the radiation at the first wavelength in comparison to any reduction in the intensity of the radiation at the second wavelength.

6. The contamination detection system of claim 5 in which the lens means has an f-number of abut 4.

7. The method of detecting contaminating material in a sample, the contaminating material having a higher coefficient of absorption of electromagnetic energy at a first wavelength than electromagnetic energy at a second wavelength, the method comprising the steps of:

directing a first radiation beam having the first wavelength along an optical axis toward the sample;

focussing the first radiation beam on a minute area of the sample to pass through that area and through any of the contaminating material located there;

reflecting at least a part of the first radiation beam back through the same area of the sample and through any contaminating material located there;

splitting the reflected first radiation beam to separate a first part of the first radiation beam reflected back through the sample from any part of the first radiation beam that did not pass through the sample;

detecting the intensity at the first wavelength of the reflected first part of the first radiation beam to form a first signal;

directing a second radiation beam having the second wavelength along an optical axis toward the sample;

focussing the second radiation beam on a minute area of the sample to pass through that area and through any of the contaminating material located there;

reflecting at least a part of the second radiation beam back through the same area of the sample and through any contaminating material located there;

splitting the reflected second radiation beam to separate a first part of the second radiation beam reflected back through the sample from any part of the second radiation beam that did not pass through the sample;

detecting the intensity at the second wavelength of the reflected first part of the second radiation beam to form a second signal; and comparing the intensity of the first signal with the intensity of the second signal.

* * * * *